United States Patent
Tanikawa et al.

(10) Patent No.: US 11,617,633 B2
(45) Date of Patent: Apr. 4, 2023

(54) METHOD AND SYSTEM FOR PREDICTING SHAPE OF HUMAN BODY AFTER TREATMENT

(71) Applicant: OSAKA UNIVERSITY, Suita (JP)

(72) Inventors: Chihiro Tanikawa, Suita (JP); Kenji Takada, Suita (JP)

(73) Assignee: Osaka University, Suita (JP)

(*) Notice: Subject to any disclaimer, the term of this patent is extended or adjusted under 35 U.S.C. 154(b) by 179 days.

(21) Appl. No.: 17/315,896

(22) Filed: May 10, 2021

(65) Prior Publication Data
US 2021/0275281 A1 Sep. 9, 2021

Related U.S. Application Data

(62) Division of application No. 15/770,461, filed as application No. PCT/JP2016/081236 on Oct. 21, 2016, now Pat. No. 11,065,084.

(30) Foreign Application Priority Data

Oct. 23, 2015 (JP) ................................. 2015-209300

(51) Int. Cl.
*A61C 7/00* (2006.01)
*G16H 30/40* (2018.01)
(Continued)

(52) U.S. Cl.
CPC .............. *A61C 7/002* (2013.01); *A61B 34/10* (2016.02); *G16H 30/40* (2018.01); *G16H 50/50* (2018.01);
(Continued)

(58) Field of Classification Search
CPC ... A61C 7/002; A61B 34/10; A61B 2034/101; A61B 2034/105; G16H 50/50; G16H 30/40; G06T 13/40
See application file for complete search history.

(56) References Cited

U.S. PATENT DOCUMENTS 8,705,875 B1    4/2014   Ricanek, Jr.
9,311,564 B2 *   4/2016   Savvides ................ G06V 40/16
(Continued)

FOREIGN PATENT DOCUMENTS

JP    2004-192378 A    7/2004
JP    2012-45247 A    3/2012
(Continued)

OTHER PUBLICATIONS

Takada, K., Yagi, M. and Horiguchi, E., 2009. Computational Formulation of Orthodontic Tooth-Extraction Decisions: Part I: to extract or not to extract. The Angle orthodontist, 79(5), pp. 885-891. (Year: 2009).*

(Continued)

*Primary Examiner* — Chuen-Meei Gan
(74) *Attorney, Agent, or Firm* — Birch, Stewart, Kolasch & Birch, LLP

(57) ABSTRACT

To have convenient and highly precise prediction of the shape of a human body after a treatment by calculation processing that includes extracting a feature vector Fnew from face data of a patient as an evaluation subject, selecting a plurality of case patients having feature vectors Fpre(i), extracted from the face data of a plurality of previous patients, obtaining pre-orthodontic facial shape models Hpre(i) and a post-orthodontic facial shape models Hpost(i) in which the faces of the selected previous case patients before and after a treatment have been normalized, obtaining a facial shape model Hnew, and obtaining a three-dimensional predicted facial shape model Hprd, by modifying the facial shape model Hnew of the patient as an evaluation subject, using a vector average difference AVEpost−AVEpre between the pre-treatment and post-treatment facial shape models.

2 Claims, 9 Drawing Sheets

(51) Int. Cl.
  *A61B 34/10* (2016.01)
  *G16H 50/50* (2018.01)
  *G06T 13/40* (2011.01)

(52) U.S. Cl.
  CPC ... *A61B 2034/101* (2016.02); *A61B 2034/105* (2016.02); *G06T 13/40* (2013.01)

(56) References Cited

U.S. PATENT DOCUMENTS

| | | | |
|---|---|---|---|
| 9,405,965 | B2 | 8/2016 | Klare |
| 10,758,322 | B2 | 9/2020 | Pokotilov |
| 10,828,130 | B2 | 11/2020 | Pokotilov |
| 2004/0136574 | A1 | 7/2004 | Kozakaya et al. |
| 2004/0197727 | A1* | 10/2004 | Sachdeva ............ A61C 7/00 433/24 |
| 2010/0271395 | A1 | 10/2010 | Isogai et al. |
| 2011/0211736 | A1 | 9/2011 | Krupka |
| 2012/0002881 | A1 | 1/2012 | Maeda |
| 2014/0379356 | A1 | 12/2014 | Sachdeva |
| 2015/0366328 | A1 | 12/2015 | Tamura et al. |
| 2016/0132720 | A1 | 5/2016 | Klare |

FOREIGN PATENT DOCUMENTS

| | | |
|---|---|---|
| JP | 2014-149677 A | 8/2014 |
| JP | 2014-171702 A | 9/2014 |
| JP | 2016-85490 A | 5/2016 |
| WO | WO 2010/041377 A1 | 4/2010 |
| WO | WO 2011/089872 A1 | 7/2011 |

OTHER PUBLICATIONS

Yagi, M., Ohno, H. and Takada, K., Nov. 2009, Decision-making models compatible with digital associative processor for orthodontic treatment planning. In 2009 IEEE Biomedical Circuits and Systems Conference (pp. 149-152). IEEE. (Year: 2009).*

International Search Report for PCT/JP2016/081236 (PCT/ISA/210) dated Dec. 6, 2016.

Takada et al., "Computational Formulation of Orthodontic Tooth-Extraction Decisions: Part I: To Extract or Not to Extract," Angle Orthodontist (2009), vol. 79, No. 5, pp. 885-891.

Tanikawa et al., "Sexual dimorphism in the facial morphology of adult humans: A three-dimensional analysis", HOMO—Journal of Comparative Human Biology 67 (2016), pp. 23-49.

Terada et al., "Image Processing and Clinical Research in Orthodontics", IPSJ SIG Technical Report, Jul. 4, 2003, pp. 133-140.

Toma et al., "Reproducibility of facial soft tissue landmarks on 3D laser-scanned facial images," Orthodontics & Craniofacial Research (2009), vol. 12, No. 1, pp. 33-42.

Translation of International Preliminary Report on Patentability issued in International application No. PCT/JP2016/081236 dated Apr. 26, 2018.

Written Opinion of the International Searching Authority for PCT/JP2016/081236 (PCT/ISA/237) dated Dec. 6, 2016.

Yagi et al., "Computational Formulation of Orthodontic Tooth-Extraction Decisions: Part II: Which Tooth Should be Extracted?" Angle Orthodontist (2009), vol. 79, No. 5, pp. 892-898.

Yagi et al., "Decision-making models compatible with digital associative processor for orthodontic treatment planning," 2009 IEEE Boimedical Circuits and Systems Conference (2009), pp. 149-152.

* cited by examiner

METHOD AND SYSTEM FOR PREDICTING SHAPE OF HUMAN BODY AFTER TREATMENT

CROSS-REFERENCE TO RELATED APPLICATIONS

This application is a Divisional of copending application Ser. No. 15/770,461, filed on Apr. 23, 2018, which is the National Phase under 35 U.S.C. § 371 of International Application No. PCT/JP2016/081236, filed on Oct. 21, 2016, which claims the benefit under 35 U.S.C. § 119 (a) to Patent Application No. 2015-209300, filed in Japan on Oct. 23, 2015, all of which are hereby expressly incorporated by reference into the present application.

TECHNICAL FIELD

The present invention relates to a method for predicting a shape of a human body after a treatment by arithmetic calculation processing, and a system therefor. In particular, the present invention relates to a method for predicting, with high precision, a shape of specific part like a facial shape of a patient after an orthodontic treatment or breast after operation, for example, and a system therefor.

BACKGROUND ART

Human face exhibits a strong influence on obtaining emotional satisfaction that he/she is socially accepted. Furthermore, the facial expression plays an important role as a non-verbal communication means for performing delivery of emotion or thought in social life. Due to such reasons, in an orthodontic dental treatment of modern days, improvement of a shape of facial soft tissue is recognized as one of the important purposes of the treatment from the standpoint of social psychology.

For example, when a treatment plan is made by a dentist for a patient having malocclusion, in order to suitably determine the treatment plan like extraction or nonextraction, or need of a surgical operation or a camouflage treatment (treatment not associated with surgical operation), or the like, it is essential to evaluate objectively the three-dimensional facial shape of a patient, and also predict the facial shape after the treatment.

Conventionally, prediction of a facial change after an orthodontic dental treatment is carried out based on profiles of a hard tissue (teeth skeleton) and a soft tissue (muscle and skin) of a patient before orthodontic treatment in which a head part X ray image (referred to as a "cephalogram" or simply as a "cephalo") is shown. For example, now widely available is a software which carries out an image processing display like move of a soft tissue following the move of a hard tissue, when the hard tissue is moved on a two-dimensional cephalo image displayed on a monitor, and thus enables visualization and simulation of a lateral view expected after the treatment.

However, the prediction algorithm using cephalo of a related art is constituted on the premise that there is a simple correlation between the movement amount of a hard tissue like tooth or jaw bone and the movement amount of a soft tissue like skin, and the correlation constant is also set based on subjective view or experiences of a professional clinician or the like. Due to such reasons, a deviation in the result of predicted facial change exists among healthcare workers, and it is not a technique of which prediction precision is guaranteed in quantitative and objective sense.

For example, disclosed in Patent Document 1 is a method for predicting facial appearance in terms of post-operative front view based on a frontal head part X ray image of a patient before operation in a surgical orthodontic treatment for a patient having jaw deformity, and a general photographic image of a face of the patient.

CITATION LIST

Patent Document

Patent Document 1: JP 2014-171702 A

SUMMARY OF THE INVENTION

Problem to be Solved by the Invention

An object of the present invention is to provide a technique allowing quantitative evaluation of a three-dimensional shape of a human body before and after a treatment and contribution to the suitable determination of a treatment plan for the patient in view of previous cases.

Means for Solving Problem

To solve the problems described above, the present invention provides a method for predicting a shape of a human body after a treatment by arithmetic calculation processing including a step of extracting multi-dimensional case feature vectors from pre-treatment three-dimensional case shape data obtained from a plurality of case patients who have received the treatment, a step of extracting a multi-dimensional patient feature vector from the three-dimensional patient shape data obtained from a patient as an evaluation subject, a step of calculating a patient shape model normalized based on the three-dimensional patient shape data of the patient as an evaluation subject, a step of selecting similar case feature vectors of a plurality of case patients that are similar to the patient feature vector from the case feature vectors, a step of calculating a plurality of pre-treatment and post-treatment similar case shape models that are normalized based on three-dimensional case shape data corresponding to the selected similar case feature vectors of the plurality of case patients, a step of calculating a vector average of the plurality of similar case shape models, a step of calculating a vector average difference between the pre-treatment similar case shape models and the post-treatment similar case shape models, and a step of modifying the patient shape model of the patient as an evaluation subject with the vector average difference and calculating a shape model as predicted after the treatment of the patient as an evaluation subject.

The present invention further provides a method for predicting a facial shape after an orthodontic treatment including a step of extracting multi-dimensional pre-orthodontic feature vectors Fpre(i) which have, as elements, a plurality of feature variables that are set in advance for a human facial shape based on pre-orthodontic three-dimensional face data of a plurality of patients who have received an orthodontic treatment, a step of extracting a multi-dimensional subject patient feature vector Fnew having the feature variables as elements based on three-dimensional face data of a new patient contemplating an orthodontic treatment (patient as an evaluation subject), a step of selecting, in a predetermined case number k, case patients having the pre-orthodontic feature vectors Fpre(i) that are related to a plurality of the patients who have received the orthodontic treatment in which the selection is made in order of the shorter distance from the subject patient feature vector Fnew, a step of calculating pre-orthodontic facial shape models Hpre (i=i1, i2, . . . , ik) as facial shape models of the each case patient in which the arrangements of feature points obtained from pre-orthodontic three-dimensional face data of the each selected case patient are normalized, a step of calculating post-orthodontic facial shape models Hpost (i=i1, i2, . . . , ik) of the each case patient in which the arrangements of feature points obtained from post-orthodontic three-dimensional face data of the each selected case patient are normalized, a step of calculating a vector average AVEpre of pre-orthodontic facial shape models Hpre (i=i1, i2, . . . , ik) of the each selected case patient, a step of calculating a vector average AVEpost of post-orthodontic facial shape models Hpost (i=i1, i2, . . . , ik) of the each selected case patient, a step of calculating a facial shape vector average difference AVEpost−AVEpre that is obtained by subtracting the vector average AVEpre of pre-orthodontic facial shape models from the vector average AVEpost of post-orthodontic facial shape models, a step of calculating a subject patient facial shape model Hnew as a facial shape model of the patient in which the arrangement of feature points obtained from the three-dimensional face data of the patient as an evaluation subject is normalized, and a step of calculating a three-dimensional predicted facial shape model Hprd as predicted after an orthodontic treatment of the patient as an evaluation subject by modifying the facial shape model Hnew of the patient as an evaluation subject with the facial shape vector average difference AVEpost−AVEpre of the each selected case patient.

The present invention further relates to a method for predicting a facial shape after an orthodontic treatment including a step of extracting multi-dimensional pre-orthodontic feature vectors Fpre(i) which have, as elements, a plurality of feature variables that are selected in advance for a human facial shape based on pre-orthodontic three-dimensional face data of a plurality of patients who have received an orthodontic treatment, a step of calculating, for classification of case data of the plurality of patients, case classes classified into a plurality of classes by carrying out clustering processing of a group of pre-orthodontic feature vectors Fpre(i) of the plurality of patients, and cluster centers Gpre(1) of the each case class, a step of extracting a multi-dimensional subject patient feature vector Fnew having the feature variables as elements based on three-dimensional face data of a new patient contemplating an orthodontic treatment (patient as an evaluation subject), a step of selecting, from a plurality of the cluster centers Gpre(1) after the clustering, a similar case class having a cluster center that has the shortest distance from the subject patient feature vector Fnew, a step of calculating pre-orthodontic facial shape models Hpre (i=i1, i2, . . . , ik) as facial shape models of the each case patient in which the arrangements of feature points obtained from pre-orthodontic three-dimensional face data of the each selected case patient belonging to the similar case class are normalized, a step of calculating post-orthodontic facial shape models Hpost (i=i1, i2, . . . , ik) of the each case patient in which the arrangements of feature points obtained from post-orthodontic three-dimensional face data of the each selected case patient belonging to the similar case class are normalized, a step of calculating a vector average AVEpre of pre-orthodontic facial shape models Hpre (i=i1, i2, . . . , ik) of each selected case patient belonging to the similar case class, a step of calculating a vector average AVEpost of post-orthodontic facial shape models Hpost (i=i1, i2, . . . , ik) of each selected case patient belonging to the similar case class, a step of calculating a facial shape vector average difference AVEpost−AVEpre that is obtained by subtracting the vector average AVEpre of pre-orthodontic facial shape models from the vector average AVEpost of post-orthodontic facial shape models, a step of calculating a subject patient facial shape model Hnew as a facial shape model of the patient in which the arrangement of feature points obtained from the three-dimensional face data of the patient as an evaluation subject is normalized, and a step of calculating a three-dimensional predicted facial shape model Hprd as predicted after an orthodontic treatment of the patient as an evaluation subject by modifying the facial shape model Hnew of the patient as an evaluation subject with the facial shape vector average difference AVEpost−AVEpre of the each selected case patient belonging to the similar case class.

According to the method for predicting a facial shape described above, it is also possible that the method further includes a step of extracting multi-dimensional pre-orthodontic cephalo feature vectors Cpre(i) which have, as elements, a plurality of feature variables that are set in advance for a human bone shape based on pre-orthodontic head part X ray images of the plurality of patients who have received an orthodontic treatment, wherein, in the step for classifying case data of the plurality of patients, the clustering processing is carried out for a group of extended feature vectors V(i) in which the pre-orthodontic feature vectors Fpre(i) and the pre-orthodontic cephalo feature vectors Cpre(i) of the plurality of patients are composited.

Furthermore, according to the method for predicting a facial shape described above, it is also possible that the method further includes a step of extracting multi-dimensional pre-orthodontic cephalo feature vectors Cpre(i) which have, as elements, a plurality of feature variables that are set in advance for a human bone shape based on pre-orthodontic head part X ray images of the plurality of patients who have received an orthodontic treatment, and a step of extracting multi-dimensional post-orthodontic cephalo feature vectors Cpost(i) based on post-orthodontic head part X ray images of the plurality of patients, in which, in the step for classifying case data of the plurality of patients, the clustering processing is carried out for a group of extended feature vectors V(i) in which the pre-orthodontic feature vectors Fpre(i), the pre-orthodontic cephalo feature vectors Cpre(i), and the post-orthodontic cephalo feature vectors Cpost(i) of the plurality of patients are composited. Furthermore, it is preferable that the extended feature vector V(i) is V(i)=[Fpre(i), Cpre(i), Cpre(i)−Cpost(i)] including, as an vector element, the cephalo feature vector difference Cpre(i)−Cpost(i) between the pre-orthodontic treatment and post-orthodontic treatment.

Furthermore, it is preferable that the method for predicting a facial shape described above further includes a step of incorporating a feature vector and/or a facial shape model obtained from the three-dimensional face data of the patient as an evaluation subject to a database.

The present invention further provides a system for predicting a facial shape after an orthodontic treatment provided with a database and a calculation processing device for carrying out calculation processing based on data memorized in the database, in which the database memorizes in advance at least multi-dimensional pre-orthodontic feature vectors Fpre(i) which have been extracted having, as elements, a plurality of feature variables that are set in advance for a human facial shape based on pre-orthodontic three-dimensional face data of a plurality of patients who have received an orthodontic treatment, pre-orthodontic facial shape models Hpre(i) in which the arrangements of feature points obtained from pre-orthodontic three-dimensional face data of the plurality of patients are normalized, and post-orthodontic facial shape models Hpost(i) in which the arrangements of feature points obtained from post-orthodontic three-dimensional face data of the plurality of patients are normalized, and the calculation processing device is provided with a means for extracting feature vector to extract a multi-dimensional subject patient feature vector Fnew having the feature variables as elements based on three-dimensional face data of a new patient contemplating an orthodontic treatment (patient as an evaluation subject), a means for selecting similar case patient to select, in a predetermined case number k, case patients having the pre-orthodontic feature vectors Fpre(i) in order of the shorter distance from the subject patient feature vector Fnew, a means for typing facial shape to calculate a vector average AVEpre of pre-orthodontic facial shape models Hpre (i=i1, i2, . . . , ik) of the each selected case patient and calculating a vector average AVEpost of post-orthodontic facial shape models Hpost (i=i1, i2, . . . , ik) of the each selected case patient, a means for modeling facial shape to calculate a subject patient facial shape model Hnew as a facial shape model of the patient in which the arrangement of feature points obtained from the three-dimensional face data of the patient as an evaluation subject is normalized, and a means for calculating a predicted facial shape model to calculate a three-dimensional predicted facial shape model Hprd as predicted after an orthodontic treatment of the patient as an evaluation subject by calculating a facial shape vector average difference AVEpost−AVEpre that is obtained by subtracting the vector average AVEpre of pre-orthodontic facial shape models from the vector average AVEpost of post-orthodontic facial shape models, and modifying the facial shape model Hnew of the patient as an evaluation subject with the facial shape vector average difference AVEpost−AVEpre of the each selected case patient.

Furthermore, a system for predicting a facial shape after an orthodontic treatment according to another embodiment of the present invention is provided with a database and a calculation processing device for carrying out calculation processing based on data memorized in the database, in which the database memorizes in advance at least multi-dimensional pre-orthodontic feature vectors Fpre(i) which have been extracted having, as elements, a plurality of feature variables that are set in advance for a human facial shape based on pre-orthodontic three-dimensional face data of a plurality of patients who have received an orthodontic treatment pre-orthodontic facial shape models Hpre(i) in which the arrangements of feature points obtained from pre-orthodontic three-dimensional face data of the plurality of patients are normalized; and post-orthodontic facial shape models Hpost(i) in which the arrangements of feature points obtained from post-orthodontic three-dimensional face data of the plurality of patients are normalized, and the calculation processing device is provided with a means for classifying case class to calculate a case class classified into a plurality of classes by carrying out clustering processing of a group of pre-orthodontic feature vectors Fpre(i) of the plurality of patients, and cluster centers Gpre(1) of the each case class, a means for extracting feature vector to extract a multi-dimensional subject patient feature vector Fnew having the feature variables as elements based on three-dimensional face data of a new patient contemplating an orthodontic treatment (patient as an evaluation subject), a means for selecting similar case class to select, from a plurality of the cluster centers Gpre(1) after the clustering, a similar case class having a cluster center that has the shortest distance from the subject patient feature vector Fnew, a means for typing facial shape to calculate a vector average AVEpre of pre-orthodontic facial shape models Hpre (i=i1, i2, . . . , ik) of the each selected case patient belonging to the similar case class and to calculate a vector average AVEpost of post-orthodontic facial shape models Hpost (i=i1, i2, . . . , ik) of the each selected case patient belonging to the similar case class, a means for modeling facial shape to calculate a subject patient facial shape model Hnew as a facial shape model of the patient in which the arrangement of feature points obtained from the three-dimensional face data of the patient as an evaluation subject is normalized, and a means for calculating a predicted facial shape model to calculate a three-dimensional predicted facial shape model Hprd as predicted after an orthodontic treatment of the patient as an evaluation subject by calculating a facial shape vector average difference AVEpost−AVEpre that is obtained by subtracting the vector average AVEpre of pre-orthodontic facial shape models from the vector average AVEpost of post-orthodontic facial shape models, and modifying the facial shape model Hnew of the patient as an evaluation subject with the facial shape vector average difference AVEpost−AVEpre of the each selected case patient belonging to the similar case.

According to the system for predicting a facial shape with the above constitution, it is also possible that the database further memorizes in advance multi-dimensional pre-orthodontic cephalo feature vectors Cpre(i) which have been extracted having, as elements, a plurality of feature variables that are set in advance for a human bone shape based on pre-orthodontic head part X ray images of the plurality of patients who have received an orthodontic treatment, and the means for classifying case class is to perform clustering processing for a group of extended feature vectors V(i) in which the pre-orthodontic feature vectors Fpre(i) and the pre-orthodontic cephalo feature vectors Cpre(i) of the plurality of patients are composited.

Furthermore, according to the system for predicting a facial shape, it is also possible that the database further memorizes in advance multi-dimensional post-orthodontic cephalo feature vectors Cpost(i) which have been extracted based on post-orthodontic head part X ray images of the plurality of patients who have received an orthodontic treatment, and the means for classifying case class is to perform clustering processing for a group of extended feature vectors V(i) in which the pre-orthodontic feature vectors Fpre(i), the pre-orthodontic cephalo feature vectors Cpre(i), and the post-orthodontic cephalo feature vectors Cpost(i) of the plurality of patients are composited. Furthermore, it is preferable that the extended feature vector V(i) is V(i)=[Fpre(i), Cpre(i), Cpre(i)−Cpost(i)] including, as an vector element, the cephalo feature vector difference Cpre(i)−Cpost(i) between the pre-orthodontic treatment and post-orthodontic treatment.

Furthermore, it is preferable that the system for predicting a facial shape further includes a means for incorporating case data to incorporate a feature vector and/or a facial shape model obtained from a three-dimensional face data of the patient as an evaluation subject to a database.

The present invention still further provides a method for predicting a breast shape after a treatment including a step of extracting multi-dimensional pre-operative feature vectors Fpre(i) which have, as elements, a plurality of feature variables that are selected in advance based on pre-operative three-dimensional breast shape data of a plurality of patients who have received an operational treatment, a step of calculating case classes classified into a plurality of classes by carrying out clustering processing of a group of pre-operative feature vectors Fpre(i) of the plurality of patients, and cluster centers Gpre(1) of the each case class, a step of extracting a multi-dimensional subject patient feature vector Fnew having the feature variables as elements based on three-dimensional breast shape data of a patient contemplating the treatment, a step of selecting, from a plurality of the cluster centers Gpre(1) after the clustering, a similar case class having a cluster center that has the shortest distance from the subject patient feature vector Fnew, a step of calculating pre-operative breast shape models Hpre (i=i1, i2, . . . , ik) as a breast shape model of the each case patient in which the arrangements of feature points obtained from pre-operative three-dimensional breast shape data of the each selected case patient belonging to the similar case class are normalized, a step of calculating post-operative breast shape models Hpost (i=i1, i2, . . . , ik) of the each case patient in which the arrangements of feature points obtained from post-operative three-dimensional breast shape data of the each selected case patient belonging to the similar case class are normalized, a step of calculating a vector average AVEpre of pre-operative breast shape models Hpre (i=i1, i2, . . . , ik) of each selected case patient belonging to the similar case class, a step of calculating a vector average AVEpost of post-operative breast shape models Hpost (i=i1, i2, . . . , ik) of each selected case patient belonging to the similar case class, a step of calculating a breast shape vector average difference AVEpost−AVEpre that is obtained by subtracting the vector average AVEpre of pre-operative breast shape models from the vector average AVEpost of post-operative breast shape models, a step of calculating a subject patient breast shape model Hnew as a breast shape model of the patient in which the arrangement of feature points obtained from the three-dimensional breast shape data of the patient as an evaluation subject is normalized, and a step of calculating a three-dimensional predicted breast shape model Hprd as predicted after operation by modifying the breast shape model Hnew of the patient as an evaluation subject with the breast shape vector average difference AVEpost−AVEpre of the each selected case patient belonging to the similar case class.

Effect of the Invention

According to the present invention, a three-dimensional shape of a face, breast, and other specific human body part of a patient before and after a treatment can be conveniently predicted with high precision according to arithmetic calculation processing in view of previous cases. As such, it can contribute to suitable determination of a treatment plan for that patient.

MODE(S) FOR CARRYING OUT THE INVENTION

First Embodiment

Figure 1:
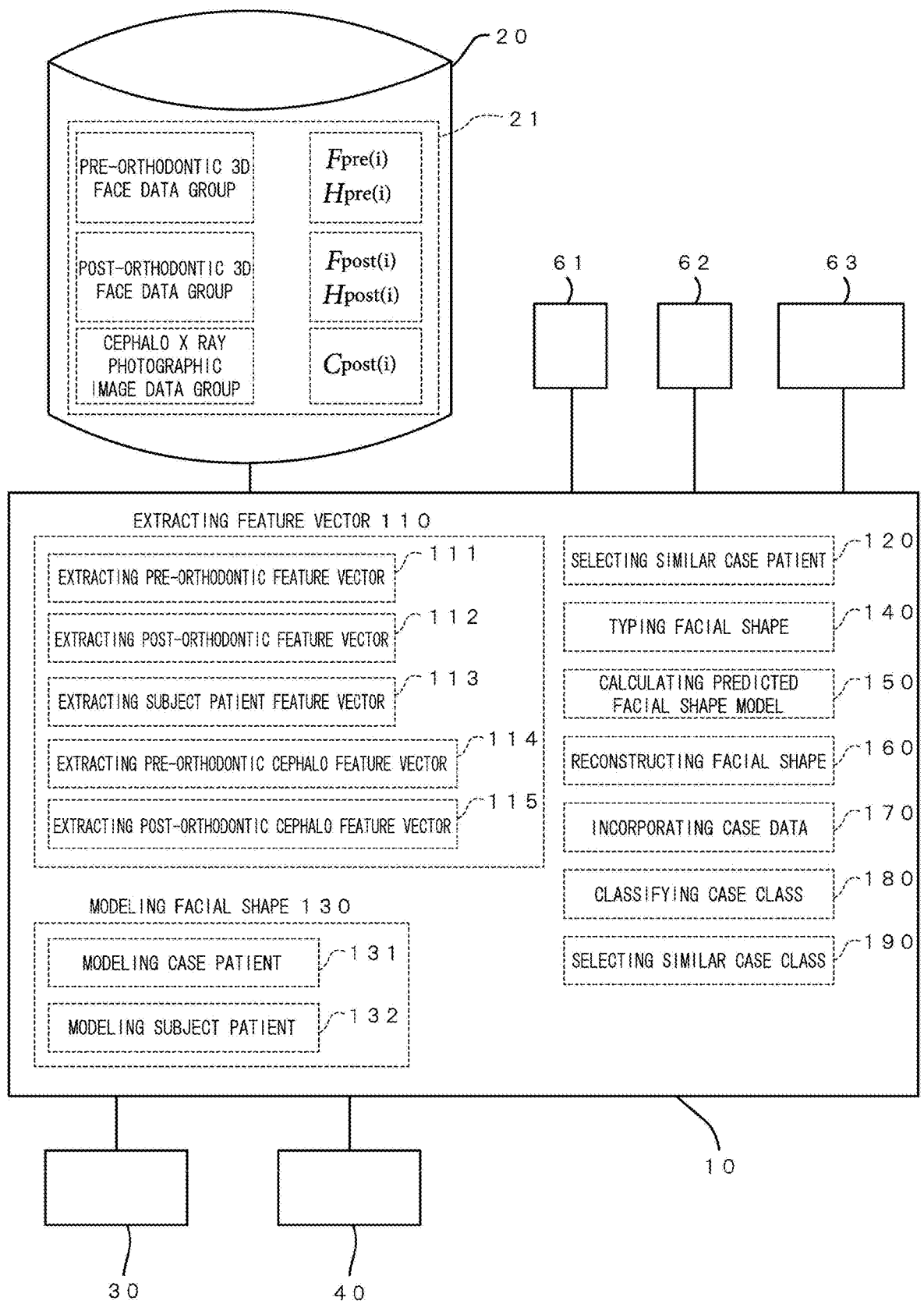
FIG. 1 is a block diagram illustrating the brief constitution of a system for predicting a facial shape.

The first embodiment of the present invention is explained. In FIG. 1, the brief constitution of a system for predicting a facial shape after an orthodontic dental treatment is exemplified. The method for predicting a facial shape according to the present invention is mainly carried out by arithmetic calculation processing by a calculation processing device 10 in the system for predicting a facial shape shown in FIG. 1, for example. However, all processings that are explained hereinbelow are not necessarily carried out by a single calculation processing device 10. Namely, as long as the problem of the present invention is solved, it is possible that case data obtained from another system or intermediate data prepared as database according to previous performing of calculation processing (specifically, feature vector, facial shape model, or the like) is utilized by the calculation processing device 10 of the system, for example. Furthermore, it is also possible that part of the processing for handling a large data like high-dimensional vector calculation processing or three-dimensional modeling processing is carried out by using a high speed host computer on network.

The calculation processing device 10 is connected with a data storage 20 with large capacity, an input device 30, and an output device 40. The data storage 20 can be, other than a hard disk or an optical disk directly connected to the calculation processing device 10, a data server in hospital which can be accessed by the calculation processing device 10 via a network. Furthermore, the data storage 20 can be installed on a wide area network, for example, a cloud data center. In the data storage 20, case data prepared as a database 21 including a X ray photographic image data or a three-dimensional face data of a patient, a facial shape feature vector or a facial shape models as intermediate data, and a predicted facial shape models as evaluation data, or the like are stored. Furthermore, it is preferable that the access to the data storage 20 or the database 21 is limited only to a special person who is allowed to share the data (for example, primary care physician).

The calculation processing device 10 is a computer device which performs calculation processing based on the data that are memorized in the data storage 20 or the database 21. The input device 30 includes a manipulation input device like keyboard, mouse, touch panel, or the like, for example. Furthermore, the input device 30 can be a device which has a function of inputting data that have been acquired or processed by another system to the calculation processing device 10 via an information memory medium or a network.

The output device 40 includes an image display for three-dimensional visual display of predicted facial shape data, for example. Furthermore, for providing intermediate data like feature vector processed by the calculation processing device 10 or evaluation data like predicted facial shape model to another system, the output device 40 can be a memory drive for memorizing those data in an information memory medium or a communication output device for outputting those data to an outside via a network.

Furthermore, the system for predicting a facial shape is constituted such that face photography data of a patient or three-dimensional face data that are taken in a hospital examination room or the like are supplied to the calculation processing device 10, either directly or via the data storage 20 or the database 21. It is acceptable that those face data of a patient are inputted to the input device 30 via an information memory medium, or inputted to the system via a hospital network, for example. The system for predicting a facial shape may also include, as a constitutional element, a digital camera 61 for taking a picture of a patient, a three-dimensional camera 62 for acquiring three-dimensional face data of a patient, or a general three-dimensional measurement device like three-dimensional scanner or laser profiler.

Memorized in the database 21 of the data storage 20 is at least the three-dimensional face data which have been obtained from image data in which pre-orthodontic treatment and post-orthodontic treatment faces of plural patients previously received an orthodontic dental treatment are photographed by the three-dimensional camera 62 or another three-dimensional measurement device. Furthermore, the case data including three-dimensional face data of each patient are classified for each item like sex, age, treatment area, treatment method, or the like of each patient, and prepared as a database. Due to such reasons, with the calculation processing device 10, case data can be searched from the database 21 by focusing on a patient as an evaluation subject for which the treatment plan is just set to be determined, and a specific patient group with similar case like same sex, same generation, same treatment area or the like.

Furthermore, according to the system for predicting a facial shape of this embodiment, it is also possible that a head part X ray image data (hereinbelow, referred to as a "cephalo") of a patient are inputted in the calculation processing device 10 and/or the data storage 20 (database 21). When the system of the present invention uses a cephalo of a patient, it is possible that the calculation processing device 10 is connected in an accessible manner to an X ray examination device (cephalo system) 63 via a hospital network, for example. It is also possible that, as case data, pre-orthodontic and post-orthodontic cephalo data of a patient who has already received an orthodontic dental treatment are kept in advance as database in the data storage 20.

The calculation processing device 10 is provided with, as a means for calculation processing to be achieved by the calculation processing, a means for extracting feature vector 110, a means for selecting similar case patient 120, a means for modeling facial shape 130, a means for typing facial shape 140, a means for calculating a predicted facial shape model 150, a means for reconstructing facial shape 160, and a means for incorporating case data 170. A means for extracting feature vector 110 includes a means for extracting pre-orthodontic feature vector 111, a means for extracting post-orthodontic feature vector 112, and a means for extracting subject patient feature vector 113. A means for modeling facial shape 130 includes a means for modeling case patient facial shape 131 and a means for modeling subject patient facial shape 132.

Figure 2:
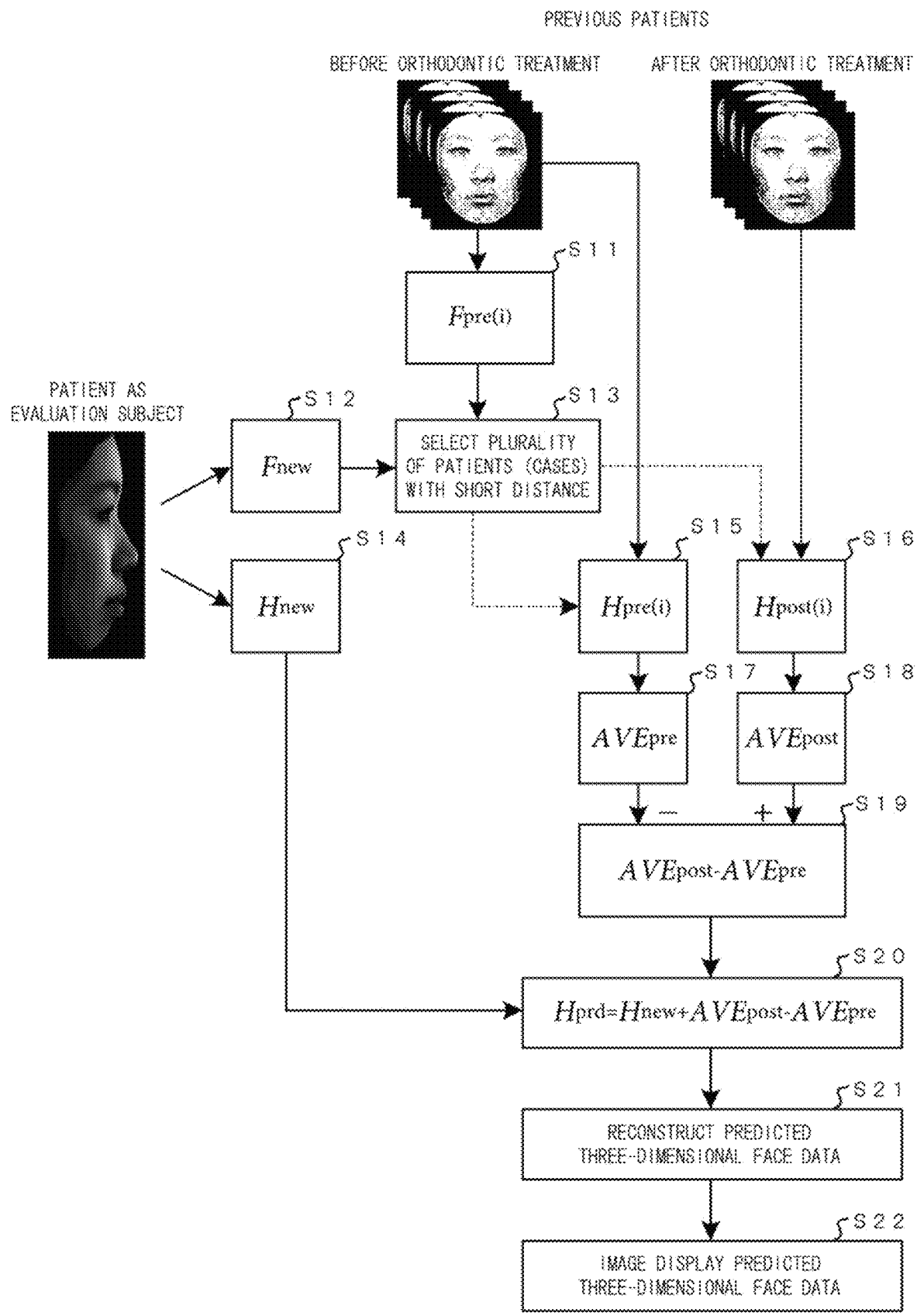
FIG. 2 is a flowchart illustrating the method for predicting a facial shape according to a first embodiment.

The first embodiment of the method consisting of the above calculating means for predicting a facial shape after an orthodontic dental treatment is explained in detail hereinbelow in view of the flowchart of FIG. 2.

First, a means for extracting pre-orthodontic feature vector 111 is to extract multi-dimensional pre-orthodontic feature vectors (pre-treatment case feature vectors) Fpre (i=1, 2, . . . , p) which have, as elements, plural feature variables that are set in advance for a human facial shape based on pre-orthodontic three-dimensional face data (case shape data) of a plurality (p people) of patients who have already received an orthodontic dental treatment (step S11).

The "three-dimensional face data" means three-dimensional coordinate data of the entire face or a pre-determined area of a patient like dental occlusion part which is acquired by the three-dimensional camera 62 or a general three-dimensional measurement device like three-dimensional scanner. The second-dimensional and three-dimensional face data may be memorized in the database 21, either as one case data of a patient or after being associated with case data of each patient. Furthermore, the face data may also include data of exhibiting at least two facial expressions of the same patient (exhibition of resting face, smiling face, or the like).

Herein, a means for extracting feature vector 110 (a means for extracting pre-orthodontic feature vector 111, a means for extracting post-orthodontic feature vector 112, a means for extracting subject patient feature vector 113) is a calculating means for finally extracting a multi-dimensional feature vector by using a feature parameters, which are geometric parameters showing the feature of a shape of a human face. The "feature parameter" indicates a geometric parameter which characteristically shows a shape of a human face, and it is selected in advance based on, for example, experiences or knowledge of professional clinicians. Herein, the feature parameters or feature variables are explained a little bit further.

Figure 3:
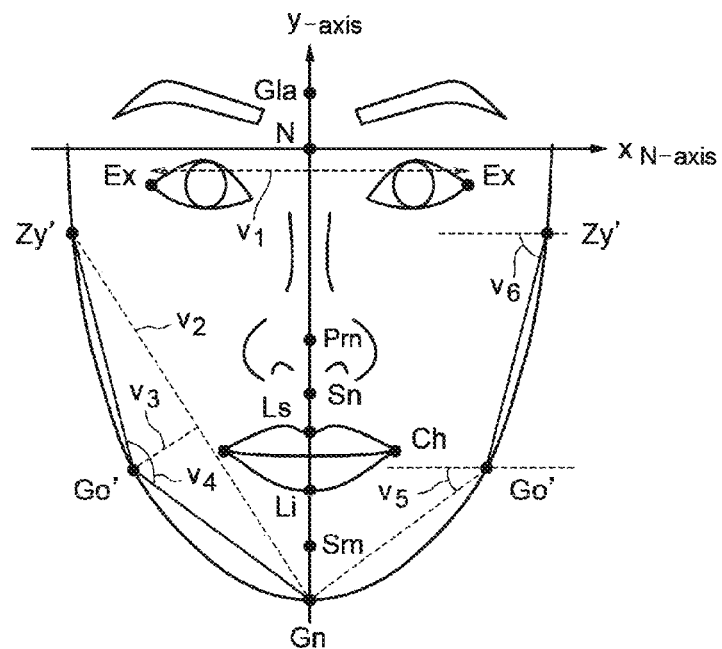
FIG. 3 is a diagram illustrating an example of selecting feature parameters that are selected from contour lines of a human face.

In FIG. 3, examples of the feature parameters that are selected from the contour lines of a human face are shown. As shown in FIG. 3, several inflection points can be recognized from a shape of a human face. Those inflection points can be selected from a corner of a boundary of an eye or a nose, the three-dimensionally most protruded area, or the most concave area. In the present specification, those inflection points are referred to as a landmark and used for defining feature parameters. Furthermore, the landmark is not particularly limited to be an inflection point, as long as it can be geometrically defined like a center point of a line which connects two inflection points, or the like.

Furthermore, the contour line of a face can be extracted as follows. First, by using a calculation program customized for measurement of a facial shape from a frontal image of a face, face normals are calculated for each pixel of three-dimensional surface data. Furthermore, the angle formed between the z coordinate and the face normals of a human face is calculated for each coordinate on face surface. Each coordinate point having 60 degrees for the angle formed between the z coordinate and the face normals of a human face is extracted, for example, and the line connecting those points is used as a facial contour line. The angle defining the facial contour line is preferably an angle between 45 degrees and 90 degrees.

One example of the feature parameter is a distance between landmarks. For example, feature parameter v1 shown in FIG. 3 is defined as a distance between eye rim Exs (|Ex-Ex|). Furthermore, like v3, it can be a distance between a line connecting landmarks (for example, line connecting the sidemost end Zy' of a face to jaw protrusion point Gn) and a landmark (for example, cheek protrusion point Go'). Furthermore, another example of the feature parameter is an angle of the line connecting landmarks. For example, the angle of feature parameter v4 is determined based on the positional relationship among the sidemost end Zy' of a face, cheek protrusion point Go', and the cheek.

Furthermore, the distance feature parameter can be a dimensionless value. For example, the width (|Ch-Ch|/|Ex-Ex|) obtained by normalization of the mouth angle width (|Ch-Ch|) with the distance between eye rims (|Ex-Ex|) can be employed as a feature parameter. Furthermore, a deviation in an average of plural values or a ratio compared to the average can be also considered as a feature parameter.

Figure 4:
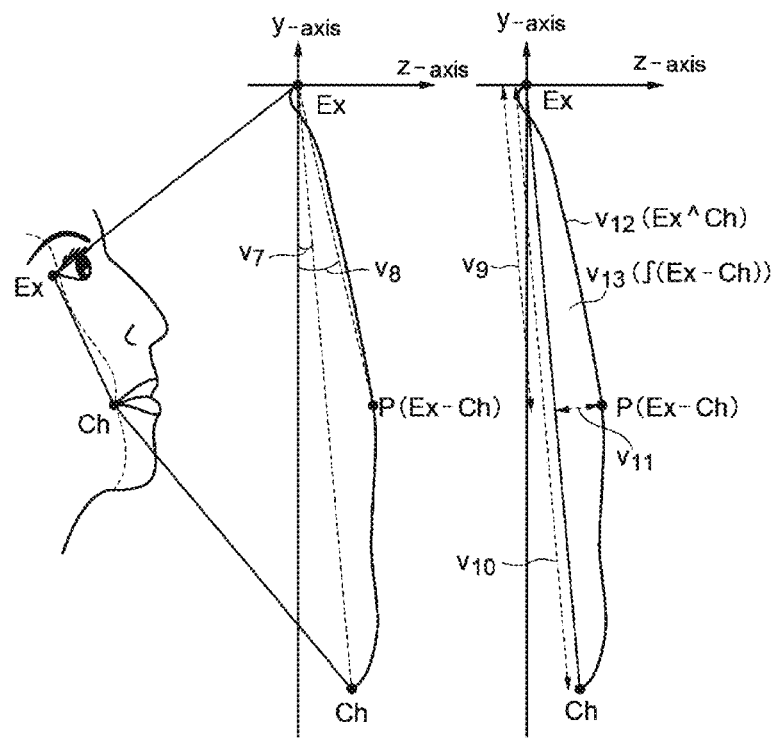
FIG. 4 is a longitudinal cross-section view illustrating an additional example of selecting feature parameters.
Figure 5:
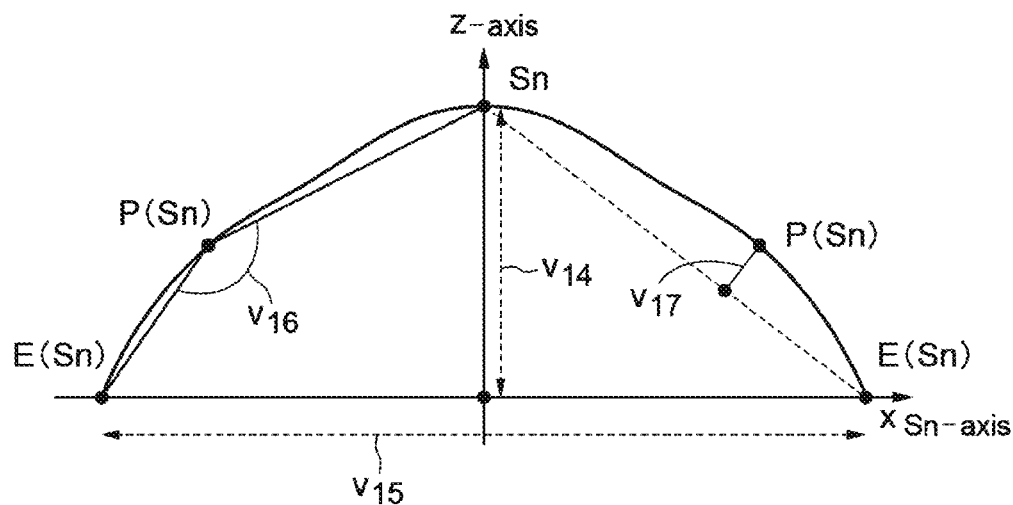
FIG. 5 is a transverse cross-section view illustrating an additional example of selecting feature parameters.
Figure 6:
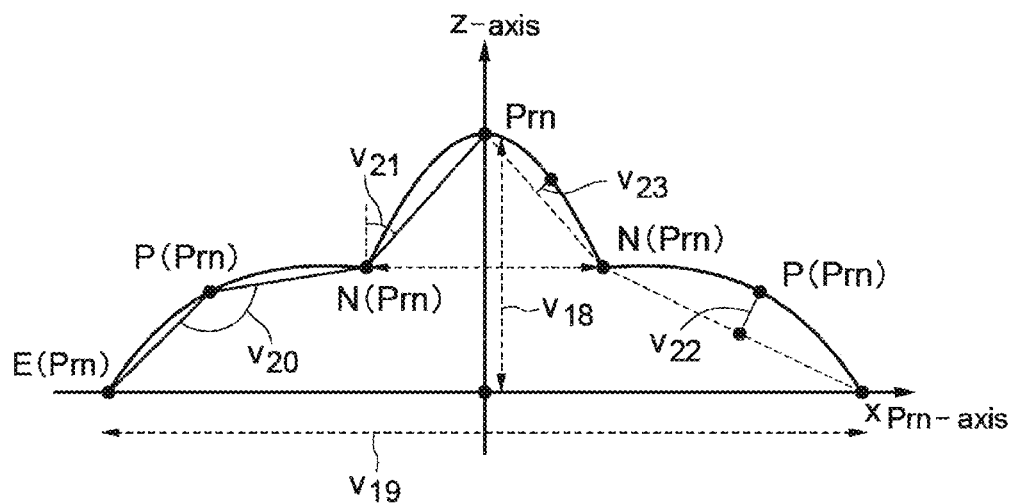
FIG. 6 is a transverse cross-section view illustrating an additional example of selecting feature parameters.

Furthermore, as shown in FIGS. 4 to 6, plural feature parameters are selected from a cross-section which is based on three-dimensional data obtained by photographing a specific area of a human face. The cross-section is obtained by data processing based on anatomical system point measurement, after determining a three-dimensional coordinate system. FIG. 4 shows, as an example, yz cross-section that is obtained by cutting a face of a testee along the line connecting eye rim Ex and mouth angle point Ch. For example, the angle (v7) in z axis direction of mouth angle Ch having eye rim Ex as a start point, the angle (v8) of cheek protrusion point P(Ex-Ch) on the cross-section having eye rim Ex as a start point, the distance (v12) of a contour line between eye rim Ex and mouth angle Ch, and the area (v13) closed by that contour line, and the like can be selected as a feature parameter.

As an additional example, xz cross-section that is obtained by cutting a face of a testee along the horizontal surface which passes through under nose point Sn is shown in FIG. 5. Similarly, in FIG. 6, xz cross-section that is obtained by cutting a face of a testee along the horizontal surface which passes through the most protruded nose point Pm is exemplified. As shown in those figures, the protrusion amount (v14, v18) in z direction of a face area, the angle of protrusion point (v16, v20), the protrusion amount (v17, v22, v23), the angle (v21) of a concave part, or the like at various cross-section positions can be selected as a feature parameter. The cross-section characterizing a facial shape can be, although not illustrated, also a cross-section which passes through a glabella point Gla, nose root point N, upper lip point Ls, lower lip point Li, or jaw end point Sm, other than those described above. Furthermore, a difference or a ratio compared to the average z value of a specific area can be added to a feature parameter.

A means for extracting feature vector 110 is to carry out processing for measuring a feature variable which corresponds to each of plural feature parameters that have been selected and set. By a means for extracting feature vector 110, thus measured a n-dimensional feature vector F=[v1, v2, v3, . . . , vn] having n feature variables as vector elements is extracted, for example. It is also possible that, from data obtained by photographing different facial expressions like resting face and smiling face, two or more feature vectors can be extracted for a single patient. Furthermore, it is also possible to extract an exhibition amount vector which has, as vector elements, a feature variables measured from facial expression exhibition data as a difference between them.

In step S11, according to the aforementioned processing, a means for extracting pre-orthodontic feature vector 111 extracts, for example, pre-orthodontic feature vectors Fpre (1) [v1, v2, v3, . . . , vn], Fpre(2) [v1, v2, v3, . . . , vn], Fpre(p) [v1, v2, v3, . . . , vn] which have n feature variables as elements, for example, from pre-orthodontic three-dimensional face data of p patients who have already received an orthodontic dental treatment.

It is also possible that, according to the same processing as described above, a means for extracting post-orthodontic feature vector 112 extracts n-dimensional post-orthodontic feature vectors (post-treatment case feature vectors Fpost(1) [v1, v2, v3, . . . , vn], Fpost(2) [v1, v2, v3, . . . , vn], . . . , Fpost(p) [v1, v2, v3, . . . , vn] from post-orthodontic three-dimensional face data (case shape data) of patients who have already received an orthodontic dental treatment.

It is also possible that feature vectors Fpre(i) and Fpost(i) are extracted by using a deep learning method. The extracted pre-orthodontic feature vectors Fpre (i=1, 2, . . . , p) and post-orthodontic feature vectors Fpost (i=1, 2, . . . , p) are incorporated, as case data for each patient, to the database 21. Furthermore, when the pre-orthodontic feature vectors Fpre(i) and post-orthodontic feature vectors Fpost(i) are already provided to the database 21, the calculation processing device 10 may carry out the subsequent processing in view of the data of the database 21 without performing processing for extracting those feature vectors.

Based on the same processing as described above, a means for extracting subject patient feature vector 113 is to extract, from three-dimensional face data (patient shape data) of a new patient contemplating an orthodontic treatment (referred to as a "patient as an evaluation subject"), an n-dimensional patient feature vector Fnew [v1, v2, v3, . . . , vn] which has the same feature variables as elements (step S12).

A means for selecting similar case patient 120 is to select, in a case number k, similar case patients having the pre-orthodontic feature vectors Fpre(i) that are related to p patients who have received the orthodontic treatment in which the selection is made in order of the shorter distance (|Fpre(i)−Fnew|) from the subject patient feature vector Fnew extracted in step S12 (step S13). Herein, the "distance" between vectors can be any of Euclid distance or Manhattan distance.

The case number k selected in step S13 is a number which is determined in advance by a professional clinician or the like. Furthermore, regarding step S13, it is preferable to select a case patient who has a shorter distance with a subject patient contemplating an orthodontic treatment in terms of pre-orthodontic feature vectors Fpre(i) that have been narrowed down to a patient having common sex, age, treatment area, or the like.

Meanwhile, the three-dimensional face data obtained by using the three-dimensional camera 62 or the like include a different number of data obtained based on a face size or the like of each patient, and have different position of an original point depending on standing position or the like of a photographed patient. In this regard, to have quantitative comparison or statistical processing of a facial shape of each patient, the system for predicting a facial shape of this embodiment is provided with a means for modeling facial shape 130 for modeling three-dimensional face data with normalized facial shape model (a means for modeling case patient facial shape 131, a means for modeling subject patient facial shape 132). A means for modeling facial shape 130 is to perform calculation processing for constructing a three-dimensional facial shape model which has been normalized by extracting pre-set anatomical feature points from three-dimensional face data of a patient and arranging the feature points on a polygon with identical number of points and identical phase geometric structure. The shape model constructed by such method is generally referred to as a "homologous model", and Homologous Body Modeling (HBM) program provided by National Institute of Advanced Industrial Science and Technology can be used, for example.

A means for modeling subject patient facial shape 132 is to calculate subject patient facial shape model (patient shape model) Hnew which is obtained by extracting anatomical feature points from three-dimensional face data of a patient as an evaluation subject (patient shape data) contemplating an orthodontic treatment and normalizing the arrangement of the feature points with a homologous model, for example (step S14).

Furthermore, a means for modeling case patient facial shape 131 is to calculate pre-orthodontic facial shape models (pre-treatment similar case shape models) Hpre (i=i1, i2, . . . , ik) which are obtained by normalizing the arrangements of the anatomical feature points obtained from pre-orthodontic three-dimensional face data of each of k similar case patients as selected in step S13 by the aforementioned modeling processing (step S15). Similarly, a means for modeling case patient facial shape 131 is to calculate post-orthodontic facial shape models (post-treatment similar case shape models) Hpost (i=i1, i2, . . . , ik) which are obtained by normalizing the arrangements of the anatomical feature points obtained from post-orthodontic three-dimensional face data of each of k similar case patients as selected in step S13 by the aforementioned modeling processing (step S16).

Herein, as case data, all of the pre-orthodontic facial shape models Hpre(i) and post-orthodontic facial shape models Hpost(i) calculated for patients may be incorporated to the database 21. Furthermore, when the pre-orthodontic facial shape models Hpre(i) and post-orthodontic facial shape models Hpost(i) of previous patients are already provided to the database 21, the calculation processing device 10 may carry out the subsequent processing in view of the model data of the database 21 without performing the modeling processing.

Subsequently, a means for typing facial shape 140 is to calculate vector average AVEpre of pre-orthodontic facial shape models Hpre (i=i1, i2, . . . , ik) of each of selected k similar case patients (step S17). Similarly, a means for typing facial shape 140 is to calculate vector average AVEpost of post-orthodontic facial shape models Hpost (i=i1, i2, . . . , ik) of each of selected k similar case patients (step S18).

Subsequently, a means for calculating a predicted facial shape model 150 is to calculate facial shape vector average difference AVEpost−AVEpre by subtracting the vector average AVEpre of pre-orthodontic facial shape model from the vector average AVEpost of post-orthodontic facial shape model (step S19). In addition, a means for calculating a predicted facial shape model 150 is to perform calculation for adding facial shape vector average difference AVEpost−AVEpre of each of selected k similar case patients to subject patient facial shape model Hnew of a patient as an evaluation subject, and thus obtaining predicted three-dimensional predicted facial shape model Hprd (=Hnew+AVEpost−AVEpre) of a patient as an evaluation subject after an orthodontic treatment (step S20).

The predicted facial shape model Hprd obtained by step S20 is just rough expression of anatomical feature points only that are predicted after an orthodontic dental treatment. As such, to have more faithful reproduction of a predicted actual facial shape, a means for reconstructing facial shape 160 is preferably to reconstruct a predicted three-dimensional face data by rearranging the anatomical feature points of predicted facial shape model Hprd in a three-dimensional face data coordinate system of a patient as an evaluation subject (step S21). Accordingly, it becomes possible to display three-dimensionally a lateral view of a face of a patient predicted after a treatment or the like on the output device 40 like image display (step S22), and thus a patient is allowed to fully understand the effect of an orthodontic dental treatment while watching the image.

With a means for incorporating case data 170, three-dimensional face data of a subject patient after the evaluation may be incorporated to the database 21. Furthermore, with a means for incorporating case data 170, pre-orthodontic subject patient feature vector Fnew extracted from the three-dimensional face data of a patient as an evaluation subject or subject patient facial shape model Hnew obtained by modeling the anatomical feature points of three-dimensional face data may be incorporated to the database 21. It is also possible that, with a means for incorporating case data 170, the post-orthodontic treatment three-dimensional face data of the patient, the post-orthodontic feature vector and/or post-orthodontic facial shape model which is extracted from the post-treatment three-dimensional face data are incorporated to the database 21. By accumulating those data in the database 21, precision of the facial shape prediction after a treatment of a future patient can be further enhanced.

Second Embodiment

Figure 7:
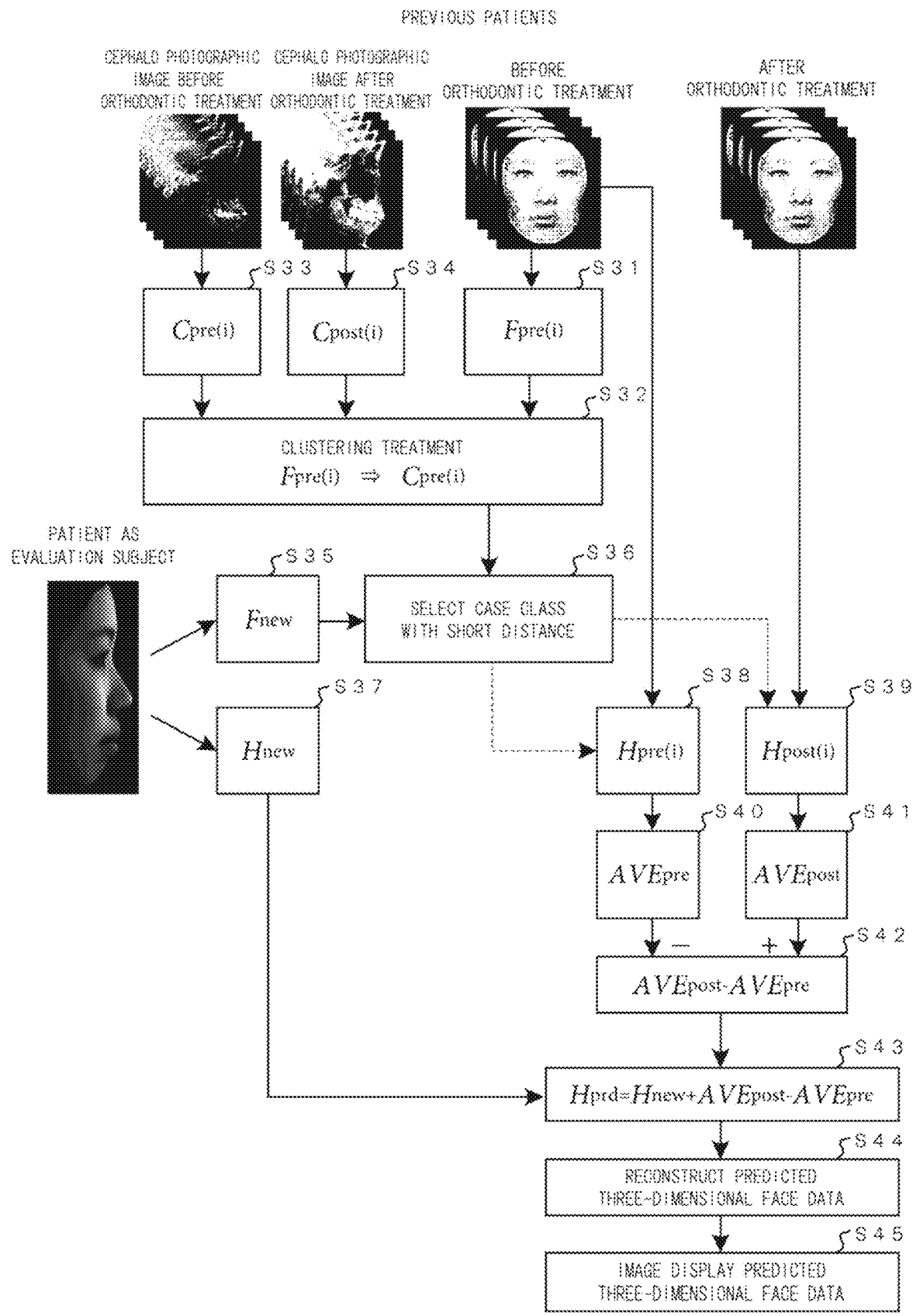
FIG. 7 is a flowchart illustrating the method for predicting a facial shape according to a second embodiment.

Next, the second embodiment of the present invention is explained in view of the flowchart of FIG. 7. Furthermore, the method for predicting a facial shape according to the second embodiment can be carried out by using the system shown in FIG. 1, similar to the first embodiment.

The calculation processing device 10 is provided with, as a means for calculation processing to be achieved by the calculation processing, a means for extracting feature vector 110, a means for classifying case class 180, a means for selecting similar case class 190, a means for modeling facial shape 130, a means for typing facial shape 140, a means for calculating a predicted facial shape model 150, a means for reconstructing facial shape 160, and a means for incorporating case data 170.

A means for extracting feature vector 110 includes a means for extracting pre-orthodontic feature vector 111, a means for extracting post-orthodontic feature vector 112, and a means for extracting subject patient feature vector 113.

A means for modeling facial shape 130 includes a means for modeling case patient facial shape 131 and a means for modeling subject patient facial shape 132.

First, a means for extracting pre-orthodontic feature vector 111 is to extract n-dimensional pre-orthodontic feature vectors (pre-treatment case feature vectors) Fpre(1) [v1, v2, v3, . . . , vn], Fpre(2) [v1, v2, v3, . . . , vn], Fpre(p) [v1, v2, v3, . . . , vn] which have, as elements, plural feature variables that are set in advance for a human facial shape, from pre-orthodontic three-dimensional face data (case shape data) of p patients, for example, who have already received an orthodontic dental treatment (step S31).

It is also possible that, according to the same processing as described above, a means for extracting post-orthodontic feature vector 112 extracts n-dimensional post-orthodontic feature vectors (post-treatment case feature vectors) Fpost(1) [v1, v2, v3, . . . , vn], Fpost(2) [v1, v2, v3, . . . , vn], Fpost(p) [v1, v2, v3, . . . , vn] from post-orthodontic three-dimensional face data (case shape data) of patients who have already received an orthodontic dental treatment, similar to above.

It is also possible that feature vectors Fpre(i) and Fpost(i) are extracted by using a deep learning method. The extracted pre-orthodontic feature vectors Fpre (i=1, 2, . . . , p) and post-orthodontic feature vectors Fpost (i=1, 2, . . . , p) are incorporated, as case data for each patient, to the database 21. Furthermore, when the pre-orthodontic feature vectors Fpre(i) and post-orthodontic feature vectors Fpost(i) of previous patients are already provided to the database 21, the calculation processing device 10 may carry out the subsequent processing in view of the vector data of the database 21 without performing processing for extracting those feature vectors.

Figure 8:
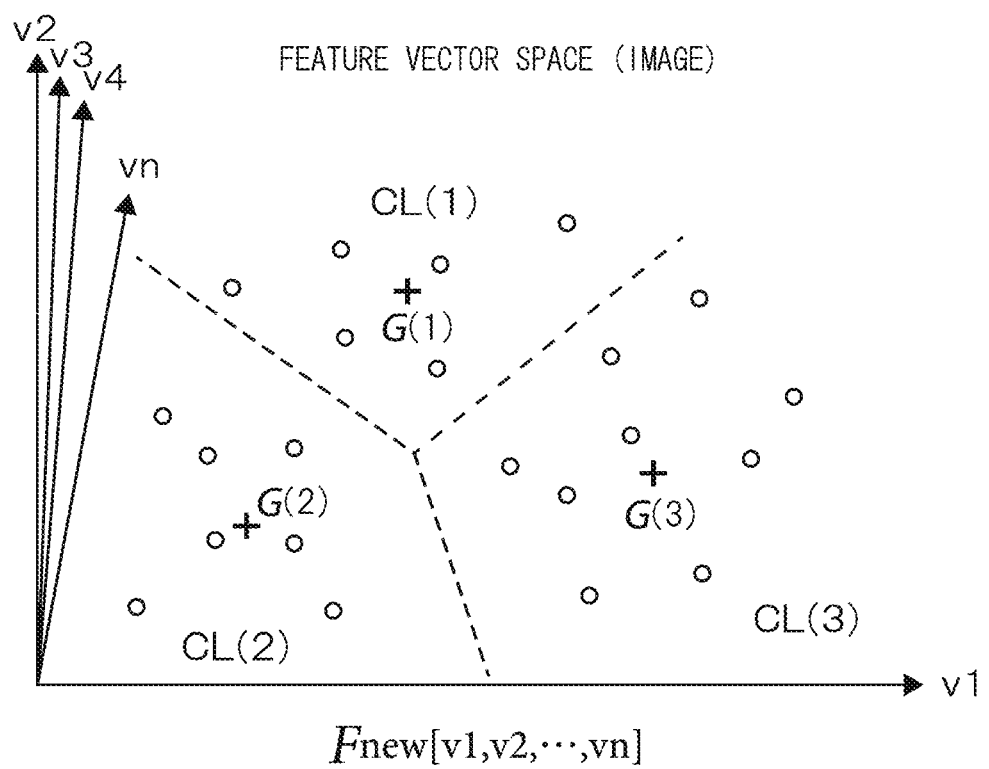
FIG. 8 is a conceptual diagram illustrating a state in which multi-dimensional feature vector spaces are clustered.

A means for classifying case class 180 is to carry out clustering processing of a group of pre-orthodontic feature vectors Fpre(i) of previous patients, calculate plural (for example, number of N) cluster centers Gpre (1=1, 2, . . . , N) for the pre-orthodontic feature vectors Fpre(i), and have classification into each case class CL (1=1, 2, . . . , N) (step S32). As the clustering processing, a general vector quantization method like Lloyd method and k-means method can be used (see, FIGS. 8 and 9).

According to k-means method, for example, clustering processing of feature vectors Fpre(i) can be carried out as described below. First, number N of the primary clusters is arbitrarily set, and virtual clusters CL*(1=1, 2, . . . , N) are allotted for n-dimensional vector space (n is the number of feature variables v). Next, according to calculation of the average of feature vectors Fpre(i) belonging to each primary cluster CL*(1), primary cluster centers G*(1=1, 2, . . . , N) are obtained. Then, the distances D*(1, i)=|G*(1)−Fpre(i)|, which are between each of obtained N centers G*(1) and all feature vectors Fpre(i), are obtained. Herein, the "distance" between vectors can be any of Euclid distance or Manhattan distance.

Next, primary cluster center G*(1) present at the shortest distance when seen from each feature vector Fpre(i) is identified, and secondary clusters CL**(1), which have as elements a group of feature vectors Fpre(i) commonly having the shortest distance center G*(1), are re-organized. Then, also for secondary clusters CL(1), secondary cluster centers G(1) are obtained, and tertiary cluster centers G***(1) are obtained from a group of feature vectors Fpre(i) at the shortest distance. Feature vectors Fpre(i) of each patient can be classified for N clusters (case classes) CL (1=1, 2, . . . , N) which have been assigned by repeating this cycle of clusters re-organization (see, FIG. 9).

It is possible that optimization processing of clusters (that is, case classes) number is subsequently carried out according to the algorithm shown below.

First, number N of clusters to be a candidate is set within a reasonable range like N=3, 4, . . . , 12, and centers GN (1=1, 2, . . . , N) of each cluster classified for each cluster number are obtained. The minimum distance DN(1)min of a distances DN(1,j) between each center GN(1), which is obtained from each cluster number N=3, 4, . . . , 12, and feature vectors Fpre(i) belonging to cluster of each center GN(1), is obtained by using the mathematical formula (1).

[Math. 1]

$$D_N(l)_{min} = \min_{j}(D_N(l, j)) \quad (1)$$

The cluster-to-cluster distance DN, which is an average of the minimum distance of each cluster, is obtained by using the mathematical formula (2).

[Math. 2]

$$D_N = \left(\sum_{l=1}^{N} D_N(l)_{min}\right) / N \quad (2)$$

$$\Delta D_N = D_{N+1} - D_N \quad (3)$$

For cluster candidates, for example, N=3, 4, . . . , 12, each of the cluster-to-cluster distance D3, D4, D12 are obtained, and N+1 that is obtained by adding 1 to N at which the variance ΔDN is at the maximum can be determined as Nopt which is the optimum cluster number.

By carrying out the above clustering processing by a means for classifying case class 180, plural cluster centers Gpre(1) can be calculated from case data of previous patients who have already received an orthodontic dental treatment, and they can be classified into each case class CL(1) (step S32).

Furthermore, according to this embodiment, a means for extracting feature vector 110 may include a means for extracting pre-orthodontic cephalo feature vector 114. In that case, a means for extracting pre-orthodontic cephalo feature vector 114 is to extract, from cephalo data acquired before an orthodontic treatment of a previous patient who has already received an orthodontic dental treatment, pre-orthodontic cephalo feature vectors Cpre(i) which have multi-dimensional feature variables as elements (step S33). In addition, regarding the processing of step S32, it is also possible that, by a means for classifying case class 180, clustering processing is carried out for a group of extended feature vectors V(i)=[Fpre(i), Cpre(i)] in which the pre-orthodontic feature vectors Fpre(i) and the pre-orthodontic cephalo feature vectors Cpre(i) of a previous patient are composited, and classifying it to each case class CL(1).

Furthermore, a means for extracting feature vector 110 may additionally include a means for extracting post-orthodontic cephalo feature vector 115. In that case, a means for extracting post-orthodontic cephalo feature vector 115 is to extract, from cephalo data acquired after an orthodontic treatment of a previous patient who has already received an orthodontic dental treatment, post-orthodontic cephalo feature vectors Cpost(i) which have multi-dimensional feature variables as elements (step S34). In addition, regarding the processing of step S32, it is also possible that, by a means for classifying case class 180, clustering processing is carried out for a group of extended feature vectors V(i) in which the pre-orthodontic feature vectors Fpre(i), pre-orthodontic cephalo feature vectors Cpre(i), and post-orthodontic cephalo feature vectors Cpost(i) of previous patients are composited. In that case, the feature vector V(i) includes the difference Cpre(i)−Cpost(i) between pre-orthodontic and post-orthodontic cephalo feature vectors in a vector element. More specifically, it is preferable that V(i)=[Fpre(i), Cpre(i), Cpre(i)−Cpost(i)].

The cephalo data of previous patients, or pre-orthodontic cephalo feature vectors Cpre(i) and post-orthodontic cephalo feature vectors Cpost(i) that are extracted from them are incorporated to the database 21. When the pre-orthodontic cephalo feature vectors Cpre(i) and post-orthodontic cephalo feature vectors Cpost(i) are already provided as case data to the database 21, the calculation processing device 10 may carry out the subsequent processing in view of the data of the database 21 without performing the calculation processing by a means for extracting feature vector 110.

Furthermore, according to the clustering processing of step S32, cluster centers Gpre(1) and the like classified from the case data of previous patients are incorporated to the database 21. When cluster centers Gpre(1) and the like are already provided as case data to the database 21, the calculation processing device 10 may carry out only the subsequent processing according to facial shape prediction of a patient as an evaluation subject without performing the clustering processing described above.

First, a means for extracting subject patient feature vector 113 is to extract an n-dimensional subject patient feature vector Fnew [v1, v2, v3, . . . , vn] which has, as elements, predetermined feature variables from three-dimensional face data (patient shape data) of a patient contemplating an orthodontic treatment (step S35).

Figure 9:
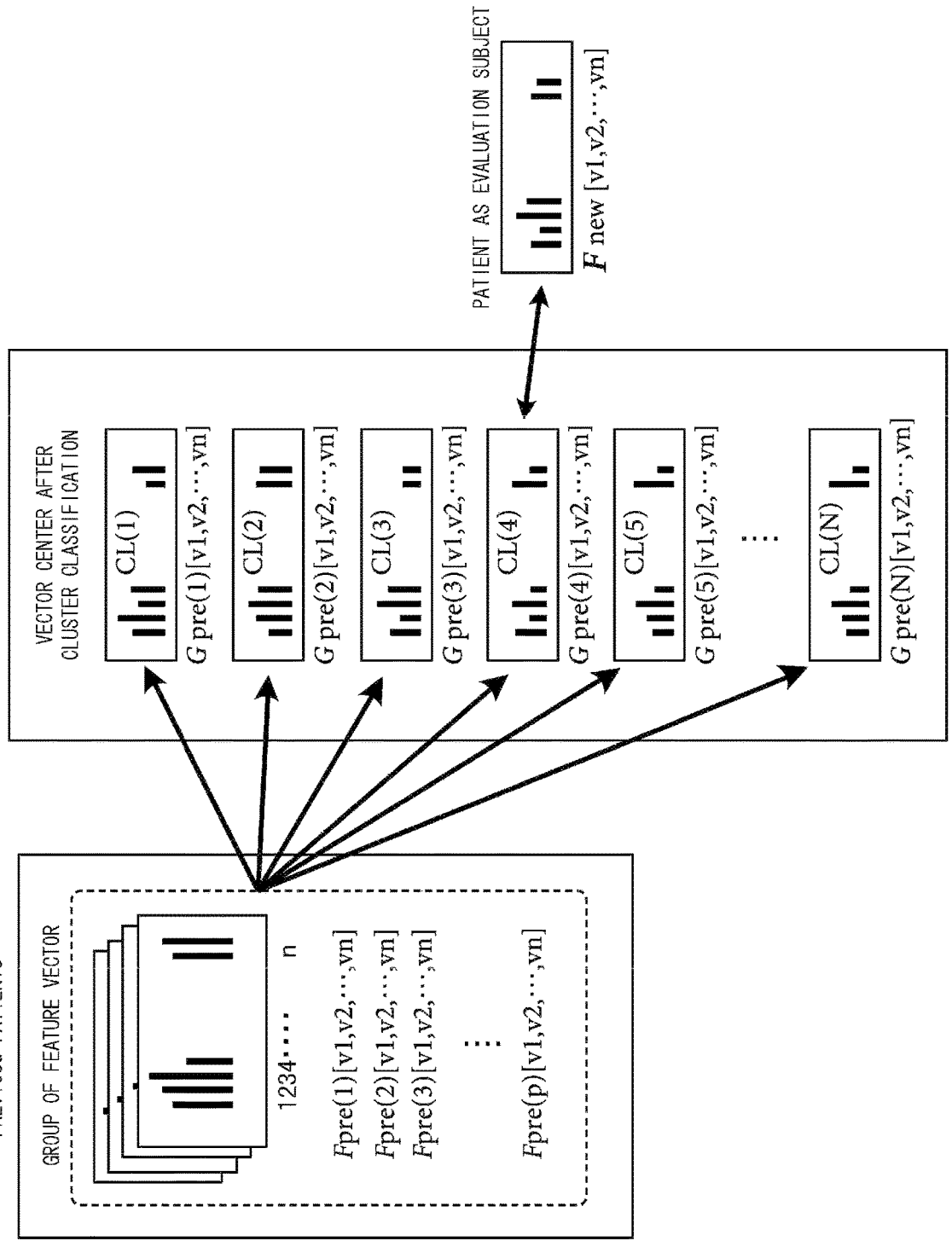
FIG. 9 is a diagram for explaining the clustering processing of a facial shape feature vector and selection of a similar case class.

A means for selecting similar case class 190 is to select, from centers Gpre(1) of pre-orthodontic feature vectors Fpre(i) belonging to each case class which has been classified by clustering processing of case data of previous patients, a similar case class CL (near) which has a vector center having the shortest distance (|Gpre(1)−Fnew|) from the subject patient feature vector Fnew (step S36; see FIG. 9). In that case, the "distance" can be any of Euclid distance or Manhattan distance.

A means for modeling subject patient facial shape 132 is to calculate subject patient facial shape model (patient shape model) Hnew which is obtained by extracting anatomical feature points from three-dimensional face data of a patient as an evaluation subject (patient shape data) and normalizing them with a homologous model, for example (step S37).

Furthermore, a means for modeling case patient facial shape 131 is to calculate pre-orthodontic facial shape models (pre-treatment similar case shape models) Hpre (i=i1, i2, . . . , ik) which are obtained by normalizing the arrangements of the anatomical feature points obtained from pre-orthodontic three-dimensional face data of each case patient belonging to similar case class CL (near) as selected in step S36 with a homologous model, for example (step S38). Similarly, a means for modeling case patient facial shape 131 is to calculate post-orthodontic facial shape models (post-treatment similar case shape models) Hpost(i=i1, i2, . . . , ik) which are obtained by normalizing the arrangements of the anatomical feature points obtained from post-orthodontic three-dimensional face data of each case patient belonging to the similar case class CL (near) with a homologous model, for example (step S39).

Herein, as case data, all of the pre-orthodontic facial shape models Hpre(i) and post-orthodontic facial shape models Hpost(i) calculated for patients may be incorporated to the database 21. Furthermore, when the pre-orthodontic facial shape models Hpre(i) and post-orthodontic facial shape models Hpost(i) of previous patients are already provided to the database 21, the calculation processing device 10 may carry out the subsequent processing in view of the model data of the database 21 without performing the modeling processing.

Subsequently, a means for typing facial shape 140 is to calculate vector average AVEpre of pre-orthodontic facial shape models Hpre (i=i1, i2, . . . , ik) of each case patient belonging to the selected similar case class CL (near) (step S40). Similarly, a means for typing facial shape 140 is to calculate vector average AVEpost of post-orthodontic facial shape models Hpost (i=i2, . . . , ik) of each case patient belonging to the selected similar case class CL (near) (step S41).

Subsequently, a means for calculating a predicted facial shape model 150 is to calculate facial shape vector average difference AVEpost−AVEpre by subtracting the vector average AVEpre of pre-orthodontic facial shape model from the vector average AVEpost of post-orthodontic facial shape model (step S42). In addition, a means for calculating a predicted facial shape model 150 is to perform calculation for adding facial shape vector average difference AVEpost−AVEpre of each patient of a similar case class to subject patient facial shape model Hnew of a patient as an evaluation subject, and thus obtaining predicted three-dimensional predicted facial shape model Hprd (=Hnew+AVEpost−AVEpre) of a patient as an evaluation subject after an orthodontic treatment (step S43).

A means for reconstructing facial shape 160 is preferably to reconstruct a predicted three-dimensional face data by rearranging the anatomical feature points of predicted facial shape model Hprd in a three-dimensional face data coordinate system of a patient as an evaluation subject (step S42). Accordingly, it becomes possible to display three-dimensionally a lateral view of a face of a patient predicted after a treatment or the like on the output device 40 like image display (step S45), and thus a patient is allowed to fully understand the effect of an orthodontic dental treatment while watching the image.

With a means for incorporating case data 170, three-dimensional face data of a subject patient after the evaluation may be incorporated to the database 21. Furthermore, with a means for incorporating case data 170, pre-orthodontic subject patient feature vector Fnew extracted from the three-dimensional face data of a patient as an evaluation subject or subject patient facial shape model Hnew obtained by modeling the anatomical feature points of three-dimensional face data may be incorporated to the database 21. It is also possible that, with a means for incorporating case data 170, the post-orthodontic treatment three-dimensional face data of the patient, the post-orthodontic feature vector and/or post-orthodontic facial shape model which is extracted from the post-treatment three-dimensional face data are incorporated to the database 21. By accumulating those data in the database 21, precision of the facial shape prediction after a treatment of a future patient can be further enhanced.

According to the method for predicting a facial shape or the system for predicting a facial shape of the embodiment described above, a three-dimensional facial shape of a patient after an orthodontic dental treatment can be predicted conveniently and highly precisely by an arithmetic calculation processing. Furthermore, because the three-dimensional facial shape of a patient to be a subject can be evaluated quantitatively, they can contribute to the suitable determination of a treatment plan for the patient in view of previous cases.

The method for predicting a facial shape and the system for predicting a facial shape according to the present invention can be also used, other than the orthodontic dental treatment, for a surgical treatment or an aesthetic improvement for a patient with jaw deformity, and the like. Furthermore, they can be used for prediction when a maxillofacial surgery (including oral surgery and plastic surgery) operation is carried out alone, or in combination with an orthodontic dental treatment or a jaw prosthetic treatment. They are also expected to be applied for predicting a change in facial shape associated with ageing.

Third Embodiment

Figure 10:
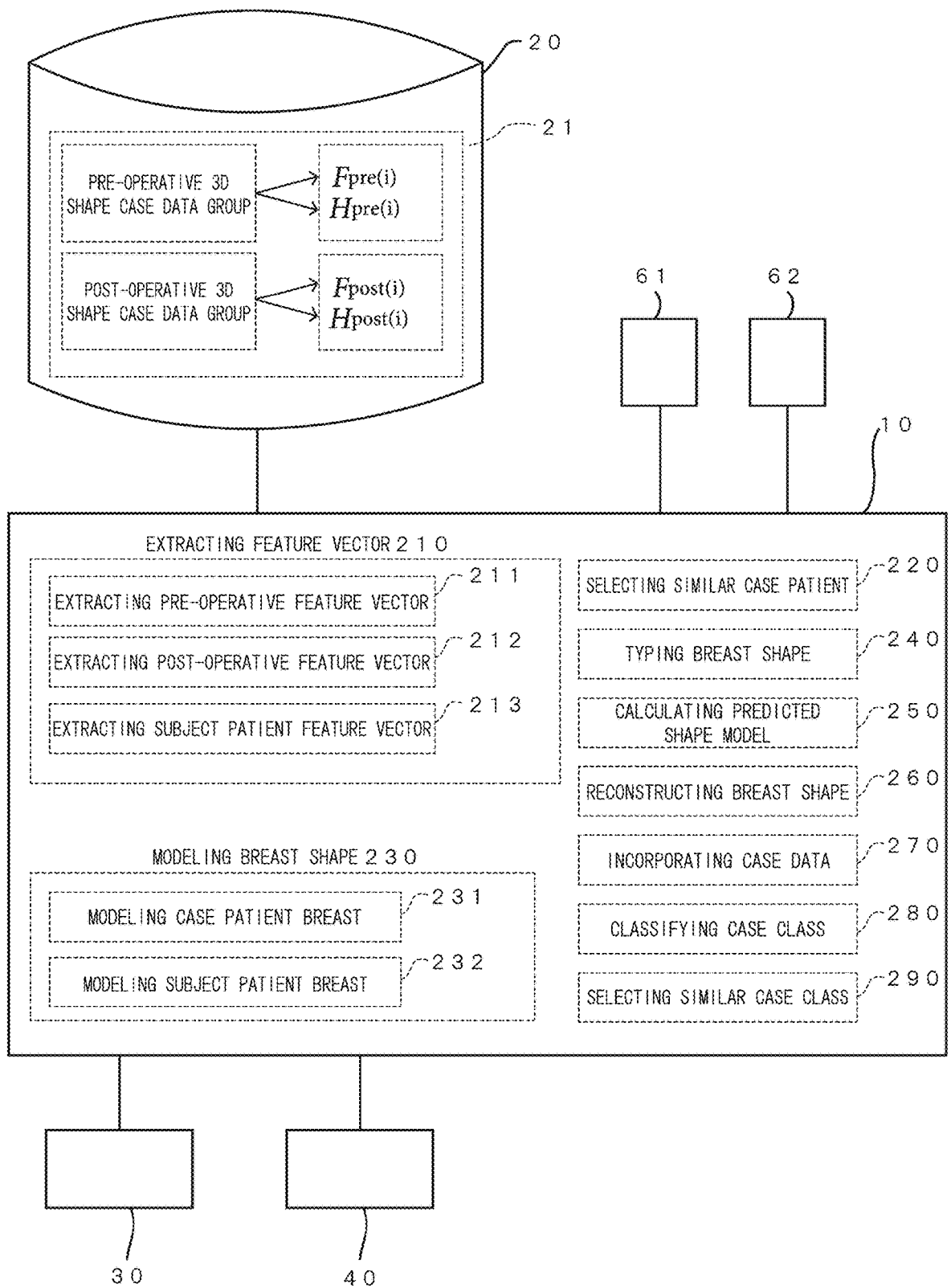
FIG. 10 is a block diagram illustrating the brief constitution of a system for predicting a breast shape as a third embodiment.

Next, the third embodiment of the present invention is explained. According to the third embodiment, a method for predicting conveniently and also highly precisely a breast shape by arithmetic calculation processing of a three-dimensional breast shape after breast cancer-related mastectomy (operation for removing breast cancer), for example, and a system used for the method are provided. In FIG. 10, a brief constitution of the system for predicting a breast shape according to this embodiment is exemplified.

The calculation processing device 10 is connected with the data storage 20 with large capacity, the input device 30, and the output device 40. Stored In the data storage 20 is a group of case data prepared as the database 21 including pre-operative and post-operative three-dimensional breast shape data (case shape data) which have been photographed from several previous breast cancer patients, feature vectors (case feature vectors) Fpre(i), Fpost(i) that are extracted from pre-operative and post-operative three-dimensional breast shape data, and three-dimensional shape models (case shape model) Hpre(i), Hpost(i) obtained by normalizing pre-operative and post-operative three-dimensional breast shape data.

The calculation processing device 10 is a computer device which performs calculation processing based on the data that are memorized in the data storage 20 or the database 21. The input device 30 includes a manipulation input device like keyboard, mouse, touch panel, or the like, for example. Furthermore, the input device 30 can be a device which has a function of inputting data that have been acquired or processed by another system to the calculation processing device 10 via an information memory medium or a network. The output device 40 includes an image display for three-dimensional visual display of predicted breast shape data, for example. Furthermore, for providing intermediate data like feature vector processed by the calculation processing device 10 or evaluation data like predicted breast shape model to another system, the output device 40 can be a memory drive for memorizing those data in an information memory medium or a communication output device for outputting those data to an outside via a network.

Furthermore, the system for predicting a breast shape is constituted such that photography data of a patient or three-dimensional data that are taken in a hospital examination room or the like are supplied to the calculation processing device 10, either directly or via the data storage 20 or the database 21. It is acceptable that those data of a patient are inputted to the input device 30 via an information memory medium, or inputted to the system via a hospital network, for example. The system for predicting a breast shape may also include, as a constitutional element, a digital camera 61 for taking a picture of a breast as a disorder area of a patient, a three-dimensional camera 62 for acquiring three-dimensional breast shape data of a patient, or a general three-dimensional measurement device like three-dimensional scanner or laser profiler.

The calculation processing device 10 according to the third embodiment is provided with, as a means for calculation processing to be achieved by the calculation processing, a means for extracting feature vector 210, a means for selecting similar case patient 220, a means for modeling breast shape 230, a means for typing breast shape 240, a means for calculating predicted shape model 250, a means for reconstructing a breast shape 260, a means for incorporating case data 270, a means for classifying case class 280, and a means for selecting similar case class 290.

A means for extracting feature vector 210 includes a means for extracting pre-operative feature vector 211, a means for extracting post-operative feature vector 212, and a means for extracting subject patient feature vector 213.

A means for modeling breast shape 230 includes a means for modeling case patient breast shape 231 and a means for modeling subject patient breast shape 232.

Figure 11:
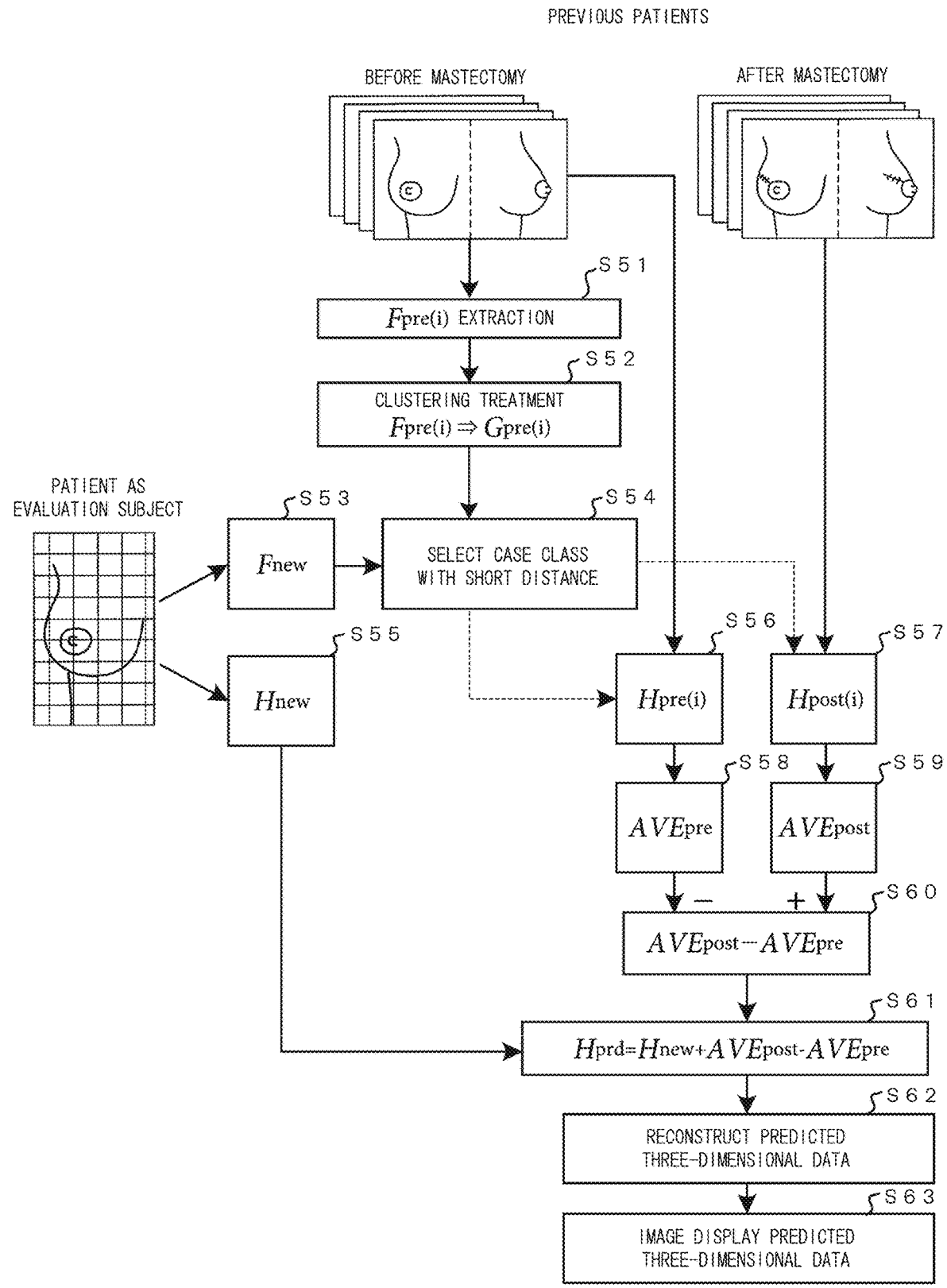
FIG. 11 is a flowchart illustrating the method for predicting a breast shape according to the third embodiment.

The method for predicting a breast shape carried out based on the aforementioned system is explained in detail in view of the flowchart of FIG. 11. First, a means for extracting pre-operative feature vector 211 is to extract n-dimensional pre-operative feature vectors (pre-treatment case feature vectors) Fpre(1) [v1, v2, v3, . . . , vn], Fpre(2) [v1, v2, v3, . . . , vn], Fpre(p) [v1, v2, v3, . . . , vn], which have, as elements, plural feature variables that are set in advance, from pre-operative three-dimensional breast shape data (case shape data before treatment) of p patients who have already received a breast cancer treatment (step S51).

According to the same processing as described above, a means for extracting post-operative feature vector 212 extracts n-dimensional post-operative feature vectors (post-treatment case feature vectors) Fpost(1) [v1, v2, v3, . . . , vn], Fpost(2) [v1, v2, v3, . . . , vn], Fpost(p) [v1, v2, v3, . . . , vn] from post-operative three-dimensional breast shape data (case shape data after treatment) of the same p patients.

It is also possible that pre-operative and post-operative feature vectors Fpre(i) and Fpost(i) are extracted by using a deep learning method. The extracted feature vectors Fpre (i=1, 2, . . . , p) and Fpost (i=1, 2, . . . , p) are incorporated, as case data for each patient, to the database 21.

A means for classifying case class 280 is to carry out clustering processing of a group of pre-operative feature vectors Fpre(i) of those case patients. In that case, case feature vectors Fpre(i) obtained after performing the same treatment as the subject patient are calculated to plural (for example, number of N) cluster centers Gpre (1=1, 2, . . . , N), and classified into each case class CL (1=1, 2, . . . , N) (step S52). As the clustering processing, a general vector quantization method like Lloyd method and k-means method can be used as described in the above (see, FIGS. 8 and 9). Furthermore, for this clustering processing, it is more preferable to supply information regarding breast shape or removed tissue amount in combination in addition to the described equation.

According to the clustering processing of step S52, cluster centers Gpre(1) and the like that are classified from case data of previous patients are incorporated to the database 21. Furthermore, when cluster centers Gpre(1) and the like are already provided as case data to the database 21, the calculation processing device 10 may carry out the subsequent processing for predicting a breast shape of a patient as an evaluation subject without performing the clustering processing of step S52.

A means for extracting subject patient feature vector 213 extracts a n-dimensional subject patient feature vector Fnew [v1, v2, v3, . . . , vn], which has a predetermined feature variables as elements, from three-dimensional breast shape data (patient shape data) of a patient as an evaluation subject who is contemplating a treatment (step S53).

A means for selecting similar case class 290 is to select, from centers Gpre(1) of pre-orthodontic feature vectors Fpre(i) belonging to each case class which has been classified by clustering processing of case data of previous patients, a similar case class CL (near) which has a vector center having the shortest distance (|Gpre(1)−Fnew|) from the subject patient feature vector Fnew (step S54). In that case, the "distance" can be any of Euclid distance or Manhattan distance.

A means for modeling subject patient breast shape 232 is to calculate subject patient breast shape model (patient shape model) Hnew which is obtained by extracting anatomical feature points from three-dimensional breast shape data of a patient as an evaluation subject and normalizing them with a homologous model, for example (step S55).

Furthermore, a means for modeling case patient breast shape 231 is to calculate pre-operative breast shape models (pre-treatment similar case shape models) Hpre (i=i1, i2, . . . , ik) which are obtained by normalizing the arrangements of the anatomical feature points obtained from pre-operative three-dimensional breast shape data of each case patient belonging to the similar case class CL (near) as selected in step S54 with a homologous model, for example (step S56). Similarly, a means for modeling case patient breast shape 231 is to calculate post-operative breast shape models (post-treatment similar case shape models) Hpost (i=i1, i2, . . . , ik) which are obtained by normalizing the arrangements of the anatomical feature points obtained from post-operative three-dimensional breast shape data of each case patient belonging to the similar case class CL (near) with a homologous model, for example (step S57).

Herein, as case data, all of the pre-operative breast shape models Hpre(i) and post-operative breast shape models Hpost(i) calculated for patients may be incorporated to the database 21. Furthermore, when the pre-operative breast shape models Hpre(i) and post-operative breast shape models Hpost(i) of previous patients are already provided to the database 21, the calculation processing device 10 may carry out the subsequent processing in view of the model data of the database 21 without performing the modeling processing.

Subsequently, a means for typing breast shape 240 is to calculate vector average AVEpre of pre-operative breast shape models Hpre (i=i1, i2, . . . , ik) of each case patient belonging to the selected similar case class CL (near) (step S58). Similarly, a means for typing breast shape 240 is to calculate vector average AVEpost of post-operative breast shape models Hpost (i=i1, i2, . . . , ik) of each case patient belonging to the selected similar case class CL (near) (step S59).

Subsequently, a means for calculating predicted shape model 250 is to calculate breast shape vector average difference AVEpost−AVEpre by subtracting the vector average AVEpre of pre-operative breast shape model from the vector average AVEpost of post-operative breast shape model (step S60). In addition, a means for calculating predicted shape model 250 is to perform calculation for adding breast shape vector average difference AVEpost−AVEpre of each patient of a similar case class to the breast shape model Hnew of a patient as an evaluation subject, and thus obtaining three-dimensional predicted breast shape model Hprd (=Hnew+AVEpost−AVEpre) of a patient as an evaluation subject after operation (step S61).

A means for reconstructing a breast shape 260 is to reconstruct a predicted three-dimensional breast data by rearranging the anatomical feature points of predicted breast shape model Hprd in a three-dimensional breast shape data coordinate system of a patient as an evaluation subject (step S62). Accordingly, it becomes possible to display three-dimensionally a breast shape of a patient predicted after an operation on the output device 40 like image display (step S63). Accordingly, the patient is allowed to fully understand the effect of the treatment.

With a means for incorporating case data 270, three-dimensional breast shape data of a subject patient after the evaluation may be incorporated to the database 21. Furthermore, with a means for incorporating case data 270, pre-operative subject patient feature vector Fnew extracted from the three-dimensional breast shape data of a patient as an evaluation subject or subject patient breast shape model Hnew obtained by modeling the anatomical feature points of three-dimensional breast shape data may be incorporated to the database 21. It is also possible that, with a means for incorporating case data 270, the three-dimensional breast shape data of the patient after a treatment, the breast shape feature vector and/or breast shape normalized model are incorporated to the database 21. By accumulating those data in the database 21, precision of the breast shape prediction after a treatment of a future patient can be further enhanced.

According to the method for predicting a breast shape or the system for predicting a breast shape which has been explained in the above, the three-dimensional breast shape of a patient after a treatment can be conveniently and highly precisely predicted based on an arithmetic calculation processing. Furthermore, because the three-dimensional breast shape of a patient to be a subject can be quantitatively evaluated, they can contribute to the suitable determination of a treatment plan for the patient in view of previous cases.

EXPLANATIONS OF LETTERS OR NUMERALS

10 Calculation processing device
21 Database
40 Output device
62 Three-dimensional camera
110 Means for extracting feature vector
120 Means for selecting similar case patient
130 Means for modeling facial shape
140 Means for typing facial shape
150 Means for calculating predicted facial shape model
160 Means for reconstructing facial shape
170 Means for incorporating case data
180 Means for classifying case class
190 Means for selecting similar case class
210 Means for extracting feature vector
220 Means for selecting similar case patient
230 Means for modeling breast shape
240 Means for typing breast shape
250 Means for calculating predicted shape model
260 Means for reconstructing breast shape
270 Means for incorporating case data
280 Means for classifying case class
290 Means for selecting similar case class
Fnew Patient feature vector
Fpre, Fpost Case feature vector
Hnew Patient shape model
Hpre, Hpost Case shape model

The invention claimed is:

1. A method for predicting a shape of a human body after a treatment by arithmetic calculation processing comprising:
a step of extracting multi-dimensional case feature vectors from pre-treatment three-dimensional case shape data obtained from a plurality of case patients who have received the treatment;
a step of classifying case shape data of the plurality of case patients into a plurality of classes by carrying out clustering processing of a group of pre-treatment feature vectors of the plurality of caser patients, and cluster centers of each case class;

a step of extracting a multi-dimensional patient feature vector from a three-dimensional patient shape data obtained from a patient as an evaluation subject;

a step of calculating a patient shape model normalized based on the three-dimensional patient shape data of the patient;

a step of selecting, from a plurality of the cluster centers after the clustering, a similar case class having a cluster center that has the shortest distance from the subject patient feature vector;

a step of calculating a plurality of pre-treatment and post-treatment similar case shape models of the selected similar case class respectively, in which the arrangements of feature points obtained from three-dimensional case shape data of each case patient belonging to the selected similar case class are normalized;

a step of calculating a vector average of the plurality of pre-treatment and post-treatment similar case shape models respectively;

a step of calculating a vector average difference between the pre-treatment similar case shape models and the post-treatment similar case shape models;

a step of modifying the patient shape model of the patient with the vector average difference and calculating a three-dimensional predicted shape model after the treatment of the patient;

determining a treatment plan for the patient based on the calculated three-dimensional predicted shape model; and displaying a three-dimensional lateral view of the patient based on the calculated three-dimensional predicted shape model.

2. A method for predicting a breast shape after a treatment comprising:

a step of extracting multi-dimensional pre-operative feature vectors Fpre(i) which have, as elements, a plurality of feature variables that are selected in advance based on pre-operative three-dimensional breast shape data of a plurality of patients who have received an operational treatment;

a step of calculating case classes classified into a plurality of classes by carrying out clustering processing of a group of pre-operative feature vectors Fpre(i) of the plurality of patients, and cluster centers Gpre(I) of the each case class;

a step of extracting a multi-dimensional subject patient feature vector Fnew having the feature variables as elements based on three-dimensional breast shape data of a new patient contemplating the treatment;

a step of selecting, from a plurality of the cluster centers Gpre(I) after the clustering, a similar case class having a cluster center that has the shortest distance from the subject patient feature vector Fnew;

a step of calculating pre-operative breast shape models Hpre (i=i1, i2, . . . , ik) as a breast shape model of the selected case patient in which the arrangements of feature points obtained from pre-operative three-dimensional breast shape data of the selected case patient belonging to the similar case class are normalized;

a step of calculating post-operative breast shape models Hpost (i=i1, i2, . . . , ik) of the selected similar case class in which the arrangements of feature points obtained from post-operative three-dimensional breast shape data of each case patient belonging to the selected similar case class are normalized;

a step of calculating a vector average AVEpre of pre-operative breast shape models Hpre (i=i1, i2, . . . , ik) of each case patient belonging to the selected similar case class;

a step of calculating a vector average AVEpost of post-operative breast shape models Hpost (i=i1, i2, . . . , ik) of each case patient belonging to the selected similar case class;

a step of calculating a breast shape vector average difference AVEpost-AVEpre that is obtained by subtracting the vector average AVEpre of pre-operative breast shape models from the vector average AVEpost of post-operative breast shape models;

a step of calculating a subject patient breast shape model Hnew as a breast shape model of the new patient in which the arrangement of feature points obtained from the three-dimensional breast shape data of the new patient as an evaluation subject is normalized;

a step of calculating a three-dimensional predicted breast shape model Hprd as predicted after operation by modifying the breast shape model Hnew of the patient with the breast shape vector average difference AVEpost-AVEpre of each case patient belonging to the selected similar case class;

determining a treatment plan for the new patient based on the calculated three-dimensional predicted breast shape model Hprd; and displaying a three-dimensional lateral view of the new patient based on the calculated three-dimensional predicted breast shape model Hprd.

* * * * *